US012498315B2

(12) United States Patent
Bao

(10) Patent No.: US 12,498,315 B2
(45) Date of Patent: Dec. 16, 2025

(54) GREY HAIR REMOVAL COMPONENT, HAIR COMB AND SYSTEM

(71) Applicant: Jianbin Bao, Edmonton (CA)

(72) Inventor: Jianbin Bao, Edmonton (CA)

( * ) Notice: Subject to any disclaimer, the term of this patent is extended or adjusted under 35 U.S.C. 154(b) by 895 days.

(21) Appl. No.: 17/428,265

(22) PCT Filed: Feb. 1, 2020

(86) PCT No.: PCT/CN2020/074142
§ 371 (c)(1),
(2) Date: Aug. 3, 2021

(87) PCT Pub. No.: WO2020/156531
PCT Pub. Date: Aug. 6, 2020

(65) Prior Publication Data

US 2022/0061491 A1 Mar. 3, 2022

(30) Foreign Application Priority Data

Feb. 3, 2019 (CN) ......................... 201910108590.2

(51) Int. Cl.
*G01N 21/25* (2006.01)
*G01N 33/483* (2006.01)
(Continued)

(52) U.S. Cl.
CPC ....... *G01N 21/255* (2013.01); *G01N 33/4833* (2013.01); *A45D 24/10* (2013.01);
(Continued)

(58) Field of Classification Search
CPC ................ A45D 24/10; A45D 26/0009; A45D 2044/007; B26B 21/12; G01N 21/255; G01N 33/4833
See application file for complete search history.

(56) References Cited

U.S. PATENT DOCUMENTS

2005/0216035 A1* 9/2005 Kraus .................. B26B 19/388
606/133
2016/0135889 A1 5/2016 Serrano Sanmiguel et al.

FOREIGN PATENT DOCUMENTS

CN 2536091 Y * 4/2002
CN 1688420 A 10/2005
(Continued)

OTHER PUBLICATIONS

Ma Machine Translation (Year: 2002).*
(Continued)

*Primary Examiner* — Rachel R Steitz
(74) *Attorney, Agent, or Firm* — Kilpatrick Townsend & Stockton LLP

(57) ABSTRACT

The disclosure provides a grey hair removal component, and a grey hair removal comb and a grey hair removal system composed of several grey hair removal components. The grey hair removal component includes at least one housing, and at least one identification unit and a grey hair removal unit arranged within the housing (0), and further includes a sensing unit arranged at an end of the housing, and the sensing unit responds to the contact of the component with a scalp and outputs a start signal; the identification unit identifies a grey hair in response to the start signal and outputs a removal signal; and the grey hair removal unit removes the identified grey hair based on the removal signal. By means of using the grey hair removal component and the grey hair removal system to scan the surface of the entire scalp (9), the aims of removing all grey hair and leaving colored hair can be achieved, and enhancing the personal appearance of a user.

20 Claims, 9 Drawing Sheets

(51) Int. Cl.
*A45D 24/10* (2006.01)
*A45D 26/00* (2006.01)
*A45D 44/00* (2006.01)
*B26B 15/00* (2006.01)

(52) U.S. Cl.
CPC .... *A45D 26/0009* (2013.01); *A45D 2044/007* (2013.01); *B26B 15/00* (2013.01)

(56) References Cited

FOREIGN PATENT DOCUMENTS

| | | | | | |
|---|---|---|---|---|---|
| CN | 203563823 | U | | 4/2014 | |
| CN | 103796606 | A | | 5/2014 | |
| CN | 104433145 | A | | 3/2015 | |
| CN | 104433147 | A | * | 3/2015 | |
| CN | 103815648 | B | * | 8/2016 | |
| CN | 205696326 | U | | 11/2016 | |
| CN | 107116580 | A | | 9/2017 | |
| CN | 208409931 | U | | 1/2019 | |
| EP | 3671556 | A1 | * | 6/2020 | ........... A45D 44/005 |
| KR | 20120039935 | A | * | 4/2012 | |
| KR | 101190485 | B1 | * | 10/2012 | |

OTHER PUBLICATIONS

Choi Machine Translation (Year: 2012).*
Wang Machine Translation (Year: 2005).*
Wang, CN-104433147-A English Translation, Nov. 27, 2024, Description (Year: 2024).*
Choi, KR-101190485-B1 English Translation, Nov. 27, 2024, Description (Year: 2024).*
The international search report mailed Apr. 24, 2020 in PCT Application No. PCT/CN2020/07 4142.

* cited by examiner

GREY HAIR REMOVAL COMPONENT, HAIR COMB AND SYSTEM

FIELD

The disclosure relates to a hair cutting system, in particular to a grey hair removal component, a grey hair removal comb and a grey hair removal system for eliminating grey hairs from their roots.

BACKGROUND OF THE DISCLOSURE

A human has about 100,000 to 110,000 hairs, with 175 to 300 hairs per square centimeter of scalp, and the growth rate of about 0.4 mm per day (C R Robbins, Chemical and Physical Behavior of Human Hair, 4th Ed, Springer-Verlag: New York, 2002). Depending on the type and content of pigments in the cortex, the hair color is also different, such as black, brown, gold, and red. With a professional distinction method, the Fischer-Saller Scale, hairs are classified to A (light)-Y (dark) and I (dark red)-VI (light red), 31 ranks in total. These different colors of hairs are collectively referred as colored hairs.

Colored hairs turn to white or grey hairs (hereinafter collectively referred to as grey hairs) to make people look old. People all over the world have conceived of many different methods, but the results are not satisfactory. For example, dyeing hair is not good for health. There are drugs suspected of regenerating colored hairs (A. Wellman et al, New Engl J Med, 347, 445, 2002), but they are not practical due to huge side effects on human body.

In fact, most people have grey hairs that are in low proportion and evenly distributed on the head. Therefore, a simple and effective method is to cut off the grey hairs directly, which has always been developed. Patent 200620121615.0 first proposes an optical-mechanical-electrical integrated cutting knife containing a comb-finger structure, which identifies grey hairs by light, and then uses an electromagnet to cut the grey hairs. In many subsequent patents, similar principles are also employed, but these disclosures have poor applicability, mainly because:

The ends of most of the comb fingers are not in contact with the scalp, but identify and cut (including burn) the grey hairs at a determined distance from the hair roots. The hairs are thin and soft, and the grey hairs that are cut from the middle instead of the roots are very easy to move with the hair comb, and intertwining with other hairs, so that the identification and cutting of the grey hairs are difficult to continue. Cutting from the middle position also inevitably produces unnecessary repeated cutting, and the additional mixing makes the whole task even more difficult. The operating schemes proposed by predecessors are too ideal to achieve the goal of removing grey hairs.

For the same reason as above, even if a part of the grey hairs can be cut off, since most of the cutting positions are some distance from the roots of the hairs, the residual grey hairs are relatively long, still affecting the personal appearance.

Therefore, there is a need for a grey hair removal component, a grey hair removal comb, and a grey hair removal system that are easy to operate and that effectively remove grey hairs.

BRIEF SUMMARY OF THE DISCLOSURE

According to one embodiment of the present disclosure, there is provided a grey hair removal component comprising at least one housing and at least one identification unit and a grey hair removal unit arranged in the housing, the component further comprising: a sensing unit arranged at the end of the housing, and the sensing unit responds to the contact of the component with the scalp and outputs a start signal; in response to the start signal, the identification unit identifies a grey hair, outputting a removal signal; and the grey hair removal unit removes the identified grey hair based on the removal signal. The present disclosure effectively solves the above-mentioned problems in the prior art by arranging the sensing unit at the end of the component housing, and can easily and quickly remove the grey hairs from hair roots while combing the hair.

In one embodiment, the housing is provided with windows at a side wall close to an end; the identification unit is configured to identify the grey hair through its window, and the grey hair removal unit is configured to remove the identified grey hair through its window.

In one embodiment, each identification unit includes a light source module, an information collection module, and an identification module.

In one embodiment, the identification module further includes one or both of a hair color identification module and a shape identification module.

In one embodiment, the grey hair removal unit uses a combination of one or more of light energy removal, force removal, electrical energy removal, magnetic energy removal, sound energy removal, or thermal energy removal to remove the identified grey hair.

In one embodiment, the grey hair removal unit includes an energy emission module and a focusing module, and the energy emission module includes a combination of one or more of light, electric, magnetic, sound, and thermal energy emission modules.

In one embodiment, the grey hair removal unit further includes a drive unit and a removal actuator, and the drive unit drives the removal actuator to protrude from the window of the housing or be kept in the housing.

In one embodiment, the driving unit includes a driving module which is an electrostatic driver, an electromagnetic driver, a piezoelectric driver or an inverse piezoelectric driver.

In one embodiment, the grey hair removal unit includes a blade that translates or rotates.

In one embodiment, the grey hair removal unit further includes a pulse generating unit for generating a voltage pulse and a microneedle for applying the pulse.

In one embodiment, the identification unit includes a first light source, an optical element, and a spectrum sensor or an image sensor, and the optical element is configured to reflect light emitted by the light source out of its window and reflect light from the window to the spectrum or image sensor.

In one embodiment, the grey hair removal unit further includes a second light source and a focusing lens, and the focusing lens focuses the light generated by the second light source to the identified grey hair to remove the grey hair.

In one embodiment, the grey hair removal unit further includes a pulse generating unit that generates a pulse in response to the removal signal, so that the first light source outputs a light beam with an intensity for removing the grey hair. In this way, the identification unit and the removal unit are integrated. When the identification unit recognizes a grey hair, the light source module increases the light intensity output by the light source to remove the grey hair.

In one embodiment, the grey hair removal component includes identification units arranged in the same housing; or arranged in adjacent housings, and the windows of the adjacent housings are arranged oppositely.

In one embodiment, the identification unit and the grey hair removal unit are arranged in the same housing; or respectively arranged in adjacent housings.

In one embodiment, the sensing unit is one or more of a contact switch, a pressure sensor, a heat inductor, an infrared sensor, a resistance detector, a capacitance detector, an electromagnetic inductor, or a sound wave recognizer.

In one embodiment, a flexible or elastic sealing material is arranged at the window of the housing.

According to one embodiment of the present disclosure, there is provided a grey hair removal component which includes a housing, one or more identification unit, and a grey hair removal unit arranged in the housing, the grey hair removal unit including a piezoelectric driver or an inverse piezoelectric driver, one end of which is fixed to the housing, and the other end of which is fixed with a blade, a microneedle or other removal actuator; or fixed with the blade or microneedle via a lever.

The present disclosure defines a person who wants to remove grey hairs as a user. The scalp of the present disclosure is the skin on and around the head with hair growing.

In embodiments of the present disclosure, windows are arranged on the side wall close to the end of the housing, and the identification unit and the grey hair removal unit of the grey hair removal component operate through the windows arranged on the housing. The various units of the grey hair removal component can be arranged in the same housing or adjacent housings. Each unit or module therein operates through the same window or windows oppositely arranged on adjacent housings on the same or corresponding area of the scalp. The same or corresponding area is called as an operation micro-area which is sized to contain a single hair follicle, or even a single hair. The use of a smaller operation micro-area can reduce the number of identified objects and the number of hairs targeted by the grey hair removal unit during each removal operation, and improving the identification accuracy and reducing the number of accidentally removed colored hairs. The length (along the moving direction of the grey hair removal component) and width (along a direction perpendicular to the moving direction) of the operation micro-area are in the range of 0.01~10 mm, in one embodiment from the diameter of the user's hair to 2 mm. Due to different races, the diameter of the hair is different. The diameter is about 0.06~0.12 mm for yellow people and black people, so a preferable range is 0.12~2 mm, while the diameter for white people is only 0.05~0.09 mm, so a preferable range is 0.09~2 mm. The identification unit identifies grey hairs in each operation micro-area, and the grey hairs are removed from the position very close to the scalp surface or from the scalp surface. Since one end of the hair is fixed to the scalp, in the method of the present disclosure, it does not need to rearrange or fix the hairs, with grey hairs directly identified and removed very conveniently. Operation is only performed on the scalp surface, which greatly reduces interference from other hairs and avoids unnecessary repeated removal. Using the hair comb of the present disclosure, in the process of combing the hair, all the grey hairs on the head of the user can be removed from the hair roots, leaving colored hair and enhancing the user's personal appearance.

Sensing Unit

In the grey hair removal component of the present disclosure, the sensing unit arranged at the end of the component housing enables the grey hair removal component to start to operate in response to the contact of the end and the scalp, which can ensure that the grey hair removal component removes a grey hair from its root, leading to the shortest remaining portion of the hair, or even to permanently remove the hair by directly destroying grey hair follicle.

The sensing unit employs a combination of one or more of light sensing, force sensing, electrical sensing, magnetic sensing, acoustic sensing, and thermal sensing to determine the contact state with the scalp. If it is confirmed that the scalp has been contacted, a start signal is generated. The function of the sensing unit is equivalent to a normally open switch. When the grey hair removal component is in contact with the scalp, the switch is closed to generate a start signal to start operation of the identification unit and grey hair removal unit.

The sensing unit can be one or more of a contact switch, a pressure sensor, a thermal inductor, an infrared sensor, a resistance detector, a capacitance detector, an electromagnetic inductor, or a sound wave recognizer. The contact switch sensing unit is physically a normally open switch. When the grey hair removal component contacts the scalp, the switch is closed and outputs a start signal. The pressure sensor sensing unit measures the pressure when the grey hair removal component contacts the scalp through a pressure sensor, and generates a start signal when the pressure is greater than a set value. The infrared sensor sensing unit measures the infrared rays emitted by the scalp through an infrared sensor, and outputs a start signal when the intensity of the infrared ray is within a set range. When the capacitive detector sensing unit is in contact with the scalp, it is equivalent to adding a large capacitor to the sensing circuit, and the change of the circuit generates a start signal. In one embodiment, a pressure sensor sensing unit is used. Another function of the pressure sensor is to alarm when the pressure is too high to prevent the user's scalp from being damaged by the excessive pressure.

Identification Unit

The identification unit includes a light source module for providing a scanning light source, an information correction module for collecting optical information in the operation micro-area, and an identification module for analyzing various information in the operation micro-area to determine the presence of grey hair in the operation micro-area. The light source module can employ a monochromatic light source or a multicolor light source, and the wavelength range is in a visible light and infrared light range, which is safe for the human body. The information collection module includes an image sensor and/or a spectrum sensor. Conventional microscopy techniques and confocal microscopy techniques can be employed for collection of optical information, or simply, non-microscopy techniques can be employed. In microscopy techniques, a concave lens or a convex lens is used to focus light. White light can be employed as a light source for collecting optical image information, and hairs can be identified by comparing the collected colors and shapes. The identification module includes a color identification module and may be a shape identification module. The color identification module determines the hair color by means of the RGB color model of the target to be tested, and a hair with RGB close to white light is determined as a grey hair, and a hair with a color deviating from white light is determined as a colored hair. The shape identification module determines the shape of the target to be determined in the operation micro-area, and if the shape of the target to be determined is regular linear, cylindrical and elliptical, the target is determined as a hair; and if the shape is an irregular shape, the target is determined as not a hair, which may actually be dandruff or dust. The elliptical cylinder here includes elliptical and oval cross-sectional cylindrical shapes.

The identification module can also employs a combination of one or more of transmission spectrum, absorption spectrum, reflection spectrum, polarization spectrum, or fluorescence spectrum to determine the hair color in the operation micro-area. In one embodiment, reflection spectrum or fluorescence spectrum is used to distinguish a colored hair from a grey hair, and light with a relatively short wavelength, such as violet light and blue light, is used for the incident light source. Since the pigment in the colored hair absorbs incident light, a colored hair is determined when the detected intensity of the reflected light is low. The incident light is absorbed by the pigment, and the luminescence intensity of protein chromophores such as tryptophan and kynurenine, that is, the fluorescence intensity, is also reduced, and thus colored hair is determined.

A grey hair can be identified by identification units combining information correction modules and spectra. Identification units are meaningful when there are hairs in the operation micro-area.

Different identification methods are selected according to different types of colored hairs. A hair close to A and VI in the Fisher-Salle scale, such as light blonde and light red hair, has less pigment content and less light absorption. It should be noted that care should be taken to exclude the interference via reflected light and other scattered light from the outer surface of the hair. If the color of the colored hair is very close to the grey hair, then the need to remove the grey hair may also be relatively low.

When the identification unit finds a grey hair in the operation micro-area, it sends out a removal signal, such as an electrical pulse signal, to notify the grey hair removal unit to remove the grey hair.

Grey Hair Removal Unit

After receiving the removal signal sent by the identification unit, the grey hair removal unit operates to remove the grey hair identified in the corresponding operation micro-area. There are two strategies for removing the grey hair: one is to permanently remove the grey hair, so that the grey hair no longer grows from there by destroying grey hair follicles; and the second one is to remove the grey hair non-permanently, leaving the grey hair follicle, and only the grey hair shaft above the scalp is removed.

The grey hair removal unit employs a combination of one or more of light energy removal, force removal, electric energy removal, magnetic energy removal, sound energy removal, or thermal energy removal to remove the identified grey hair.

The removal unit includes an energy emitting module that emits high-intensity light energy, electrical energy, magnetic energy, sound energy, and thermal energy, and a focusing module for concentrating these energy to local points or areas of grey hairs.

A laser or a high-power light-emitting diode is employed as the energy emission module for the light energy removal, and the generated light pulses are focused by the focusing module, to cut off the grey hair via vaporization or destroy hair follicle from the root. The visible light source and infrared light source are preferred, which are safe for the human body.

In the electrical energy removal or magnetic energy removal, electric, magnetic or electromagnetic field pulses is employed to generate a sufficiently high energy density at grey hair roots to remove the grey hair. Restricting high energy to a local operating area not only reduces energy consumption, but is also safe for the human body. For example, partial spark discharge is employed to cut off the grey hair, and electrolysis is employed to destroy hair follicles, and so on.

In the sound energy removal, the cavitation effect via ultrasonic waves is utilized to generate high-sound-intensity ultrasonic pulses at the grey hair root to remove the grey hair.

In the thermal energy removal method, the temperature at the local area of the grey hair root is increased, and removing the grey hair.

Because the cross section area of the hair is small and requires a high energy density, the grey hair is also removed by a combination method for combining several different kinds of energy, such as a combination of electromagnetic waves and lasers. Scented gas may be produced when removing the grey hair, so a negative pressure suction system can be provided.

In the force removal, a force is used to cut the grey hair, and the removal unit includes a driving module that generates and controls a driving force and a cutting actuator that changes positions and performs cutting based on the driving force.

The drive module is an electric driver or a magnetic driver, such as an electrostatic drives, an electromagnetic drives, a piezoelectric drives or an inverse piezoelectric drives, and the cutting actuator is a blade, scissors or a microneedle electrode. The angle of the cutting actuator can be adjusted, may be perpendicular to the hair shaft of the grey hair root. The cutting actuator is flexible or elastic, and changes direction during cutting, such as changing the up and down movement to the left and right movement.

In one embodiment, a piezoelectric driver or an inverse piezoelectric driver is used to control the microneedle electrode or blade. The inverse piezoelectric effect has the characteristics of fast response speed (up to a microsecond level), high displacement accuracy and long service life. In one embodiment, a piezo bending actuator bends in response to a voltage pulse, driving the cutting actuator to cut off a grey hair. In another embodiment, a stack multilayer piezo actuator stretches in response to voltage pulses to drive a flexible or elastic cutting actuator to cut off the grey hair.

The grey hair removal component can be wrapped by a housing, the upper end of the housing is connected with other grey hair removal components or fixed with an external device, and the lower end is in contact with the scalp when use. In the component, the windows for providing an operation micro-area for the identification unit and the grey hair removal unit are arranged adjacent to the contact area of the sensing unit, that is, in the outer area of the lower end head of the housing. The flexible or elastic sealing material can be arranged at the side and/or bottom of the lower end head to prevent tiny particles such as hair, dandruff and dust from entering the grey hair removal component.

The sensing unit, the identification unit and the grey hair removal unit can be combined arbitrarily.

The operation micro-areas corresponding to the identification unit and the grey hair removal unit are the same or different. Generally speaking, when the sensing unit contacts the scalp in the vicinity of the identification unit and the removal unit, the goal is achieved to remove a grey hair from its root, and the operation micro-areas corresponding to the identification unit and the removal unit should overlap as much as possible. However, at a given moment, the operation micro-areas corresponding to the two units can also be different. For example, the identification unit is arranged in the front, with the removal unit in the back, and a lag response time is preset for the removal unit, to remove the grey hair identified by the identification unit, especially when the grey hair removal component performs scanning at a constant speed. Such a design can enable a shorter length of the operation micro-area.

Arranging identification units at the front and back positions or opposite sides adjacent to the removal unit is valuable for improving the removal of grey hair, especially when an operation micro-area contains hairs.

When the grey hair removal component is operating, the lower end head contacts the scalp surface at a large angle, and the end head has a variety of different shapes and structures. In one embodiment, the selection of the shape thereof as required and reasonably set each unit in the housing, so that the grey hair removal component can accurately and quickly identify and remove the grey hair. The following are several preferred solutions.

The first one is a square end head, which has a right-angled cross-section in the width direction. The square end head allows the grey hair removal component to contact the scalp in a large area, so there is more space to arrange three units, and enabling the identification unit and removal unit closer to the scalp, and the shorter residual roots of the grey hairs. With the square end head, only the grey hairs beside the grey hair removal component can be removed, while the grey hairs in the scalp area covered by the end head itself cannot be removed. In one embodiment, the smaller the width, the better the square end head will be, which can increase the proportion of the scanning area.

The second one is a tapered or conical end head, which has a tapered cross-section in the width direction. With the tapered end, all the hairs are arranged on both sides of the grey hair removal component and would not be covered, but a significantly improved accuracy is required for identifying and removing grey hairs in the length direction. The portion of the tapered end head that directly contacts the scalp is small, and the identification unit and the removal unit sometimes have to be placed far away from the scalp, for example, when grey hairs are removed by a force, the residual roots of grey hairs are slightly longer than with a square end head.

The third one is a semi-conical and semi-square end head, which has a tapered shape on one side of the cross-section in the width direction and a right-angled shape on the other side.

Grey Hair Removal Comb

According to another embodiment of the present disclosure, there is provided a grey hair removal comb, comprising a body and at least one grey hair removal comb finger, and the grey hair removal comb finger includes the grey hair removal component as described above.

In one embodiment, the grey hair removal comb includes grey hair removal components as described above, and the grey hair removal unit in each grey hair removal component removes the identified grey hair based on the removal signal from the identification unit in the grey hair removal component; or the grey hair removal unit in each grey hair removal component removes the identified grey hair based on the removal signals from the identification units in the other grey hair removal components.

In one embodiment, the windows on the housing of the comb fingers are arranged toward the adjacent comb fingers.

In one embodiment, the spacing between the comb fingers at the middle portion of the comb fingers is greater than that between the comb fingers at the end.

In one embodiment, the grey hair removal comb further includes comb fingers which are arranged at intervals with the grey hair removal comb fingers. Different from grey hair removal comb fingers, the comb fingers here can be comb fingers of a conventional comb.

Due to the large number of hairs, in order to improve efficiency, grey hair removal components are combined into a grey hair removal system for use, with no limit to the form and number of combinations.

A common combination manner is to arrange the grey hair removal components in an array to form a grey hair removal comb. By using one or more housings as comb fingers, grey hair removal components each form a part of the comb finger of the grey hair removal comb. The comb fingers can be fixed with each other, for example, being connected side by side at the upper portion of the grey hair removal component, or fixed on the comb body.

In one embodiment, the comb fingers are fixed by arranging in a row at equal intervals, and the finger ends are in the same straight line.

The identification unit and grey hair removal unit may be arranged on the same comb finger or on adjacent comb fingers. Identification units are arranged around the operation micro-area corresponding to the removal unit, for example, the identification unit is arranged on the adjacent position of the removal unit and on the adjacent comb finger on the opposite side, to better identify grey hair.

In one embodiment, the distance between comb fingers is greater at the area far from the end, such as the middle area, than in the end area. This can be achieved by changing the shapes of the comb fingers to allow the rest of the hairs (including grey hairs not on the surface of the scalp) to pass through smoothly.

In one embodiment, the grey hair removal comb fingers are arranged alternately with the conventional comb fingers. Conventional comb fingers have a small width with no removal unit arranged inside, but the removal units are arranged in the grey hair removal comb fingers on both sides of the removal unit, and are staggered back and forth along the scanning direction.

Different from the previous single row of comb fingers, arranging the grey hair removal comb fingers in two or more rows in parallel can improve efficiency for users with short hair.

The grey hair removal comb is powered by a power supply module arranged in the comb body of the grey hair removal comb, and an external power source may also be used.

Further, the grey hair removal comb includes a hair dispenser or a hair pressing plate to guide the hair near the end of the fingers. The grey hair removal comb also includes a hair lifter, which is a hair roller or a conventional comb used to lift up fallen hairs. Compared to yellow people, white people and black people often have curly hair, and the hair lifter can also straighten their hair.

The grey hair removal comb can be used directly. A user only needs to hold the grey hair removal comb, press the finger ends to the scalp surface at a large angle, and then move the grey hair removal comb like a conventional comb to remove the grey hair.

Digital Control Grey Hair Removal System

According to another embodiment of the present disclosure, there is provided a digital control grey hair removal system, which includes: a controlled robotic arm; a digital control subsystem for controlling the robotic arm to scan at a determined speed and direction; and at least one grey hair removal component as described above arranged on the robotic arm.

In one embodiment, the grey hair removal component is movably connected with the robotic arm.

In one embodiment, the digital control subsystem further drives movement of each grey hair removal component based on a signal from a sensing unit in the grey hair removal component, so that the end of each grey hair removal component is in contact with the skin, and improving the grey hair removal efficiency.

In one embodiment, the digital control subsystem further includes a removal unit for removing the positions of the user's head and the grey hair removal component; a posture control unit generating a posture adjustment control signal for the robotic arm body according to the positional relationship between the user's head and the grey hair removal component; a trajectory control unit controlling the movement trajectory of the grey hair removal component according to the positional relationship between the user's head and the grey hair removal component.

In one embodiment, the digital control subsystem includes positioners and transceiver units.

In one embodiment, the digital control grey hair removal system further includes an auxiliary robotic arm for combing hair.

In one embodiment, the grey hair removal component maintains a large angle relative to the scalp when scanning the head.

The positioner includes at least three signal transmitting/receiving points, which can be fixed in the areas below the hair of the user's head and above the chin, such as ears, zygomatic arch, cheekbones, nose, eyebrow arch, and forehead area. Signal transmitting/receiving points are fixed on the grey hair removal component or grey hair removal comb.

At fixed places, such as ceilings, walls and floors, signal transmitting/receiving base points are fixed. Signal transmitting/receiving point communicates with the signal transmitting/receiving base point by using electromagnetic waves or light signals, and position data of the signal transmitting/receiving point is determined according to the direction, intensity and phase of the electromagnetic waves or light.

In one embodiment, two robotic arms are employed, and a second auxiliary robotic arm is used for combing hair. For example, the auxiliary robotic arm can pull up and straighten the hair, making it easier to identify and remove the hair.

The auxiliary robotic arm can be connected with a conventional comb. According to actual position data of a user's head and the grey hair removal component or the grey hair removal comb, the digital control subsystem commands the two robotic arms to cooperatively remove the grey hair.

The grey hair removal component or the grey hair removal comb only contacts with the scalp. They are connected to the robotic arm body with a movable joint, and when they are entangled or wrapped with the hair, they can be disconnected from the robotic arm body in time. The grey hair removal component or the grey hair removal comb is powered by the robotic arm body, and is not powered after disconnection. The robotic arm body stops moving when it encounters resistance.

Furthermore, cameras are arranged on the robotic arm body and the grey hair removal component to facilitate users to monitor their operating status. The entire system is equipped with a power-off module and a power-off button to power off the entire system when necessary. The lower portion of the robotic arm is a safe area, facilitating detachment by users.

The digital control grey hair removal system enables more flexible use of the sensing unit, identification unit and grey hair removal unit of the grey hair removal component.

Digital Control Method for Removing Grey Hair

In the method, the aforementioned grey hair removal component is utilized to sense the scalp in a digital positioning or scanning manner, to obtain a collection of three-dimensional coordinate data of the entire scalp surface, and the identification unit and the removal unit respectively distinguish hair color and remove grey hair by using the collection of three-dimensional coordinate data as digital scan coordinates.

In one embodiment, the identification unit first performing scanning, records three-dimensional coordinates of roots of all grey hairs, and then the digital control subsystem commands the removal unit to remove these grey hairs. The advantage of using digital control technology is to enable grey hair removal processes after completing one grey hair scanning.

Furthermore, by the digital control technology, the proportion of grey hairs and a map of the grey hair distribution area can be draw. The user can decide whether and how to remove the grey hair according to his/her own preference. When the user chooses to permanently remove grey hair, it is best to use the digital control grey hair removal system, because by the technology, the grey hair removal component or the grey hair removal comb can be controlled to have a short pause, to more thoroughly destroy grey hair follicles. The beneficial effects of the present disclosure are as follows:

During different stages of life, according to personal preferences, the purpose of removing grey hair is different. When the grey hair initially emerges, the number of grey hairs is small, and the user can choose to remove these grey hairs permanently or non-permanently. The biggest advantage of permanent grey hair removal is convenience, but the destruction of hair follicles can only target a small number of grey hairs. With the increase in the number of grey hairs, a more reasonable choice for users is to remove grey hairs non-permanently. When the user needs hair in the future, for example, when the number of hair is insufficient due to hair loss, it makes sense to retain enough hairs, even if grey hairs.

If users prefer short hair styles, it is relatively easy to remove a grey hair, because a short grey hair is more upright and easier to be removed, and a short colored hair does not interfere with grey hair removal. Since in the present disclosure, a grey hair is removed from the root, even with a short hair style, the user can maintain a good personal appearance of not seeing the grey hair as long as the user removes the grey hair that grows in time, just like a male user shaves his beard every day.

If users prefer long hair styles, it is best to comb their hair in advance.

To sum it up:

1. The present disclosure proposes a practical and feasible method for removing grey hair. By providing a sensing unit at the end of the housing of the grey hair removal component, the component starts to identify and remove the grey hair only when it contacts the scalp, and the grey hair can be removed at its root, and overcoming difficulties about cutting and combing due to performing hair cutting at a distance from the scalp, as well as the difficulty of automatically removing the grey hair.
2. The present disclosure employs a controlled scanning technology to achieve full coverage of the user's scalp and remove all the grey hairs on the user's head.
3. Because the grey hair is removed from the root, only the colored hair is left on the head after the user removes the grey hair, and the user's personal appearance can be really enhanced due to completely invisible grey hairs.

The present disclosure is not only applicable to head hair, but also applicable to any other hairs, including eyebrows, beard, armpit hair, pubic hair, chest hair, back hair, arm hair, leg hair or the like.

BRIEF DESCRIPTION OF THE DRAWINGS

The embodiments of the present disclosure will be described in further detail below in conjunction with the figure.

DETAILED DESCRIPTION OF THE DISCLOSURE

Figure 1:
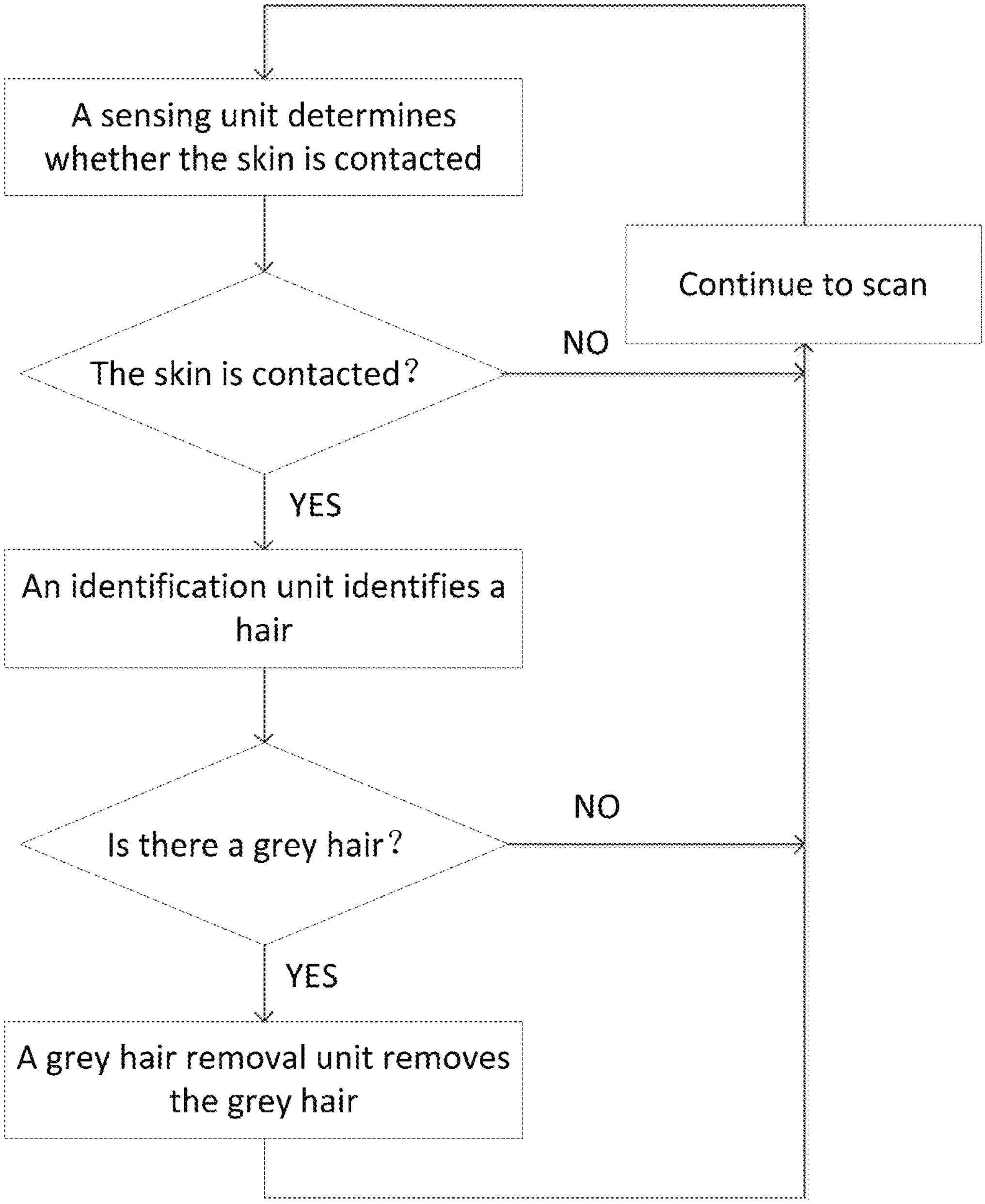
FIG. 1 shows a schematic diagram of the grey hair removal process.

In order to explain the present disclosure more clearly, the present disclosure is further described below in combination with preferred embodiments and the figure. Similar components in the figures are denoted by the same reference numerals. The content described below is illustrative rather than restrictive, and should not be used to limit the protection scope of the present disclosure.

Figure 2:
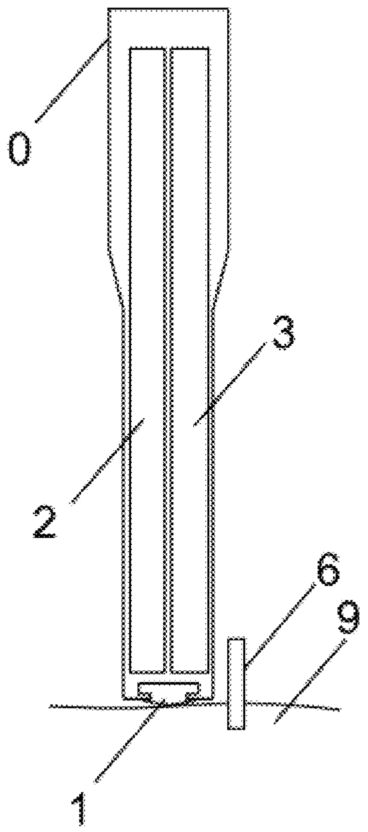
FIG. 2 shows a schematic diagram of a grey hair removal component according to a first embodiment of the present disclosure.

Hereinafter, a preferred embodiment of the grey hair removal component according to the present disclosure will be described in detail with reference to FIGS. 1 to 4. The present disclosure is a grey hair removal component including a housing 0, a sensing unit 1 arranged at the end of the housing, an identification unit 2 and a grey hair removal unit 3 arranged in the housing (as shown in FIG. 2, each unit in the figure is illustrative, not expressing their shapes or mutual positional relationships), and window(s) (not shown) arranged on the side wall near the end of the housing. The window(s) may be an opening formed on the side wall (including the side end), or a window(s) may be formed at the opening. The sensing unit of the grey hair removal component of the present disclosure located at the end of the housing outputs a start signal when it contacts the scalp. Each identification unit includes a light source module, an information correction module, and an identification module. The identification unit responds to the start signal, the light emitted by the light source module illuminates the operation micro-area through the light path and the window on the housing, the collection module collects the reflected light from the operation micro-area and transmits it to the information collection module through the light path, and the identification module identify the image or spectrum from the information collection module, determine whether the determined object is a grey hair, and output a removal signal when a grey hair is identified. The grey hair removal unit removes the identified grey hair based on the removal signal. By combing or scanning the entire scalp surface, the grey hair on the user's head can be removed from its root, leaving the colored hair. FIG. 1 shows a flow chart in the case where a control unit is to control the automatic scanning via the grey hair removal component.

The following examples illustrate the units of the grey hair removal component and the grey hair removal system combined by the grey hair removal component.

First Embodiment: Sensing Unit

FIG. 2 shows a grey hair removal component including a sensing unit 1 according to the present disclosure. The sensing unit is one or more of a contact switch, a pressure sensor, a thermal inductor, an infrared sensor, a resistance detector, a capacitance detector, an electromagnetic inductor, or a sound wave recognizer.

In a one embodiment, a pressure-sensing sensing unit is used. The pressure sensor 1 housed in the housing 0 is used to sense the pressure when the component is in contact with the scalp 9. When the pressure sensor 1 is in contact with the scalp 9, the pressure increases. When the pressure is greater than a set value, outputting a start signal. The grey hair removal component starts to identify a hair 6.

In another embodiment, a contact switch sensing unit is used. The sensing unit may include a movable member and a normally opened switch. When the grey hair removal component is in contact with the scalp 9, the movable member moves upward, closes the normally open switch, and outputs a start signal. The grey hair removal component starts to identify the hair 6.

Second Embodiment: Identification Unit

Figure 3A:
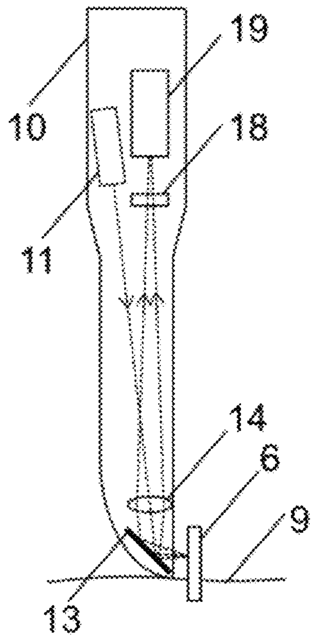
FIG. 3*a*-3*c* show schematic diagrams of grey hair removal components according to a second embodiment of the present disclosure.
Figure 3B:
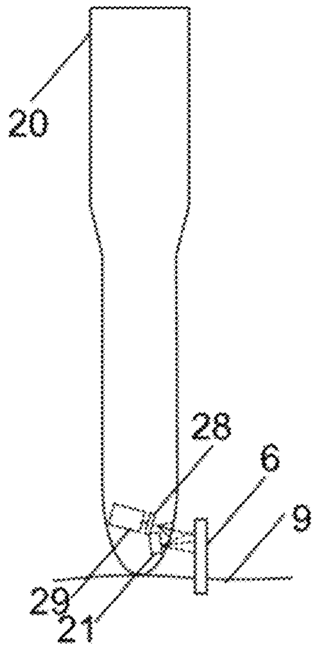
Figure 3C:
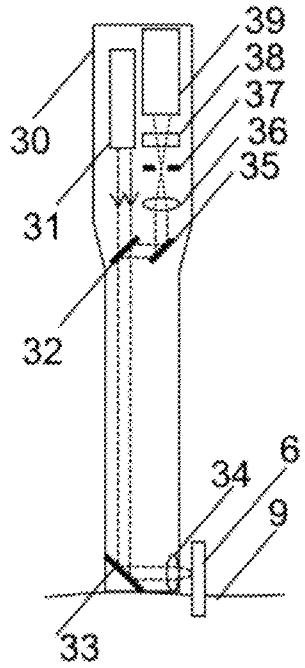

The identification unit in the grey hair removal component of the present disclosure includes a light source, an information collection module and an identification module. FIGS. 3*a*-3*c* show schematic diagrams of grey hair removal components including an identification unit according to a second embodiment of the present disclosure.

In the embodiment shown in FIG. 3*a*, the signal correction module employs traditional microscopy technology, and the end of the housing is drawn with a semi-cone and semi-square end head as an example. In the identification unit of the component 10, the white light emitted by the light source 11 is reflected by the reflector 13 and illuminates the hair root 6 on the scalp surface 9 from the side window of the housing, the light reflected by the hair 6 enters the information collection module, for example, a CCD image sensor 19, through the reflector 13, and the focusing lens 14 and the identification module identify a grey hair based on collected optical data information for the operation micro-area.

Continuing to refer to FIG. 3*a*, in another embodiment, traditional microscopy technology is employed for the signal correction module. In the identification unit of the component 10, the light emitted by the light source 11 illuminates the root of the hair 6 in the scalp surface 9 from the side, the light reflected by the hair or fluorescence passes through a reflecting lens 13, a focusing lens 14, and a filter 18, and then enters the information collection module such as a detector 19, which detects the light intensity. The identification module identifies a grey hair according to the light intensity. If the intensity is higher than a predetermined intensity, a grey hair is determined, and if the intensity is lower than the predetermined intensity, a colored hair is determined or no hair is in the operation micro-area.

In the preferred embodiment with reference to FIG. 3*b*, the signal correction module employs non-microscopic technology and is drawn with a tapered end head as an example. A small light source 21, a filter 28 and a detector 29 are directly arranged at the bottom area of the component 20. The light emitted by the light source 21 illuminates the hair root 6 on the scalp surface 9 from the side, and the reflected light of the hair 6 or fluorescence passes through the filter 28 and enters the detector 29, and the identification module identifies the grey hair according to the detected light intensity.

In the embodiment with reference to FIG. 3*c*, the signal correction module employs confocal microscopy technology and is drawn with a square end head as an example. In the component 30, the light emitted by a purple light source 31 passes through the transflective dichroic lens 32, illuminates the root of the hair 6 on the scalp surface 9 from the side, the fluorescent light emitted by the hair 6 passes through the focusing lens 34 and the reflecting lens 33 (the sequence of the two can be interchanged), and then the fluorescent light reflected by the dichroic lens 32 passes through a reflecting lens 35, a focusing lens 36, a small hole 37 and a filter 38, and finally enters a detector 39 which detects the fluorescence intensity, and the identification module identifies the grey hair according to the fluorescence intensity.

Third Embodiment: Grey Hair Removal Unit

The grey hair removal unit in the grey hair removal component of the present disclosure employs a combination of one or more of light energy removal, force removal, electrical energy removal, magnetic energy removal, sound energy removal, or thermal energy removal to remove the identified grey hair. FIGS. 4*a*-4*h* show schematic diagrams of grey hair removal components including grey hair removal units according to a third embodiment of the present disclosure.

Figure 4A:
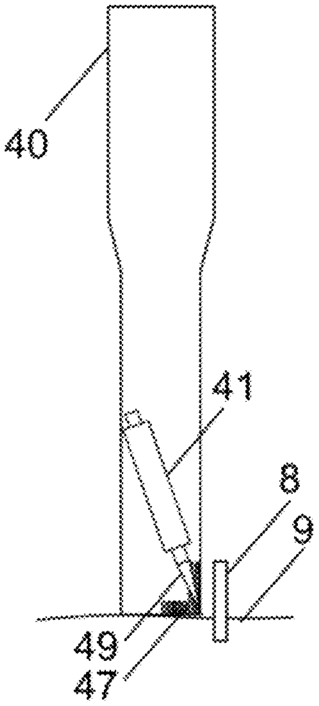
FIG. 4*a*-4*h* show schematic diagrams of grey hair removal components according to a third embodiment of the present disclosure.
Figure 4B:
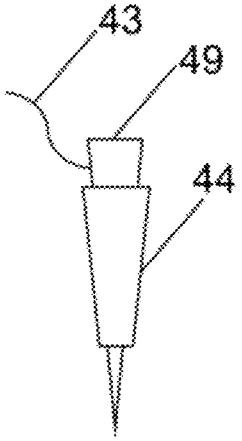

In the embodiment with reference to FIGS. 4*a* and 4*b*, when the removal unit in the component 40 receives the removal signal sent by the identification unit, a microneedle electrode 49 is driven by an electromagnet or a piezoelectric body 41 such as a stack multilayer piezo actuator and is drawn by a square end head as an example, and the microneedle electrode penetrates into the scalp 9 through the window. A puncture depth is 1~2 mm into the hair follicle of grey hair 8. Applying a voltage pulse to the microneedle electrode 49 can permanently destroy the hair follicle of the grey hair 8. The voltage pulse generated by the pulse generating unit is applied to the microneedle electrode 49 through a wire 43, as shown in FIG. 4*b*, the portion of the microneedle electrode 49 above the scalp is protected by an insulator 44. The flexible sealing material 47 is arranged near the side bottom window of the module 40 to prevent fine particles such as hair, dandruff and dust from entering the module 40.

Figure 4C:
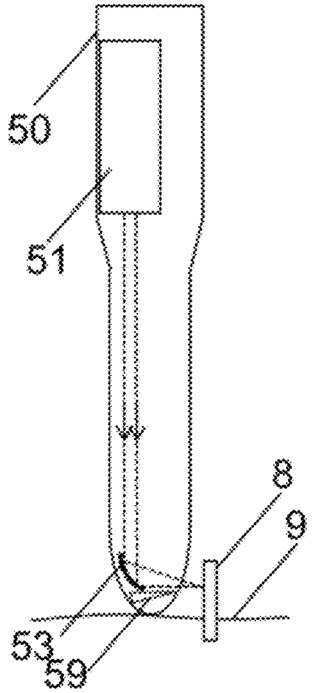

In the embodiment with reference to FIG. 4*c*, when the removal unit in the component 50 receives the removal signal sent by the identification unit, a high-power laser light source 51 generates light pulses at a high-intensity, and the light energy is focused to the root of the grey hair 8 by using a focusing lens, such as a concave lens 53, to cut off the grey hair 8 at the focal point (as shown in FIG. 4*c*, drawn with a tapered end head as an example).

In another embodiment with reference to FIG. 4*c*, when the removal unit in the component 50 receives the removal signal sent by the identification unit, the light source 51 generates a light pulse at a high-intensity, which is focused to the root of the grey hair 8 by a concave lens 53. At the same time, an electrode 59 releases an RF electrical pulse (the ground electrode is the wall surface of the adjacent cell, not shown). Light energy and electric energy operate together to cut off the grey hair 8 on the scalp surface 9.

Figure 4D:
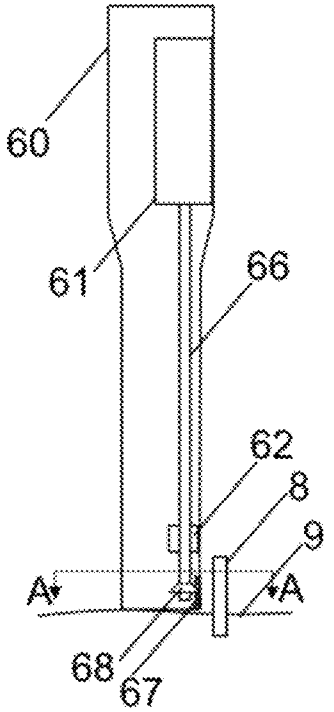
Figure 4E:
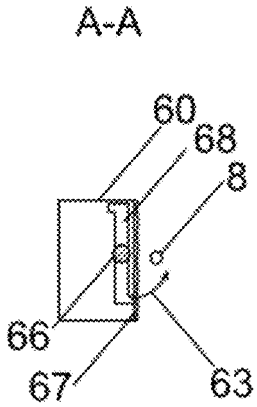

In the embodiment with reference to FIGS. 4*d* and 4*e*, when the removal unit of the component 60 receives the electrical pulse sent by the identification unit, a micro stepping motor 61 drives a cutter rod 66 to rotate in a semicircle, which is drawn with a square end head as an example. The distal end of the rod 66 is supported by a bearing 62, and a blade 68 fixed on the cutter rod 66 cuts off the grey hair 8 on the scalp surface 9 during rotation (a rotation direction 63, as shown in FIG. 4*e*). The sealing material 67 is fixed to the side bottom of the housing of the removal unit 60.

Figure 4F:
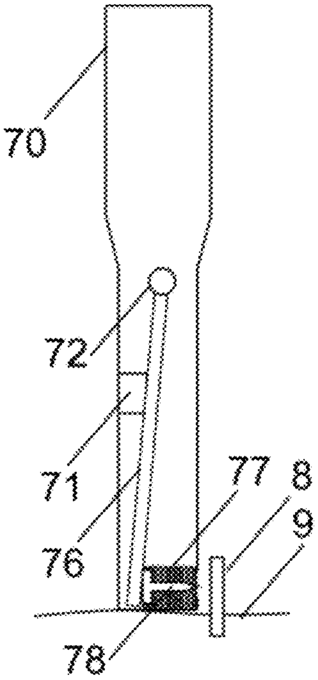

In the embodiment with reference to FIG. 4*f*, when a removal unit of a component 70 receives the removal signal sent by the identification unit, an electromagnet or piezoelectric body 71, such as a stack multilayer piezo actuator, is triggered to operate, and drive a lever 76 fixed by a fulcrum 72 to move toward the right. A blade 78 is wrapped by an elastic sealing material 77 except for the tip of the blade, and the lever 76 pushes the blade 78 to move to the right through the window to cut the grey hair 8 on the scalp surface 9 (as shown in FIG. 4*f*, a square end head is drawn as an example). Subsequently, the elastic sealing material 77 rebounds to drive the lever 76 and the blade 78 to reset. The elastic sealing material 77 is tightly sealed against the housing at the bottom of the side of the removal unit 70.

Figure 4G:
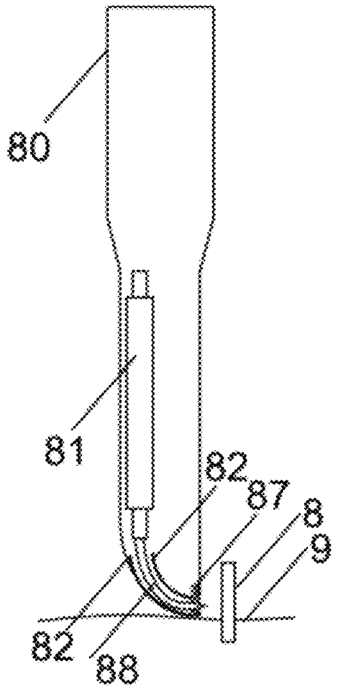

In the embodiment with reference to FIG. 4*g*, when a removal unit of a component 80 receives the removal signal sent by the identification unit, an electromagnet or piezoelectric body 81, such as a stack multilayer piezo actuator, is triggered to start operation, the top end is moved down to drive the flexible blade 88 to turn under the guide groove 82 or the housing of the removal unit 80 (as shown in FIG. 4*g*, drawn with a semi-conical and semi-square end head as an example), and the blade 88 quickly moves to the right and cuts the grey hair through the window 8. Then the electromagnet or piezoelectric actuator 81 drives the blade 88 to reset. The flexible sealing material 87 is arranged on the side bottom of the removal unit 80.

Figure 4H:
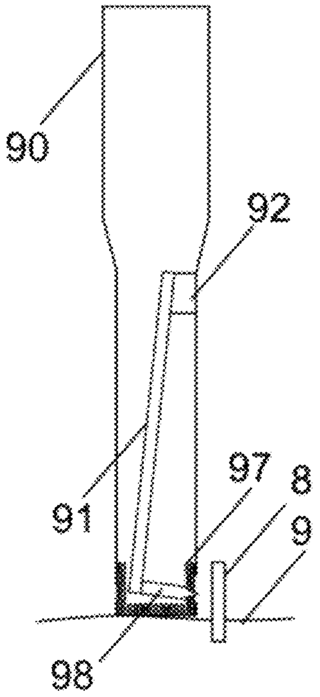

In the embodiment with reference to FIG. 4*h*, when the removal unit of the component 90 receives the electrical pulse sent by the identification unit, the piezoelectric body 91, such as the piezoelectric bending actuator, fixed by the fixing material 92, is triggered to bend to the right under the voltage (as shown in FIG. 4*h*, drawn with a square end head as an example), and the lower end is displaced to directly drive the blade 98 to move to the right. The blade 98 cuts off the grey hair 8 after being squeezed against the adjacent housing through the window. Subsequently, the piezoelectric actuator 91 drives the blade 98 to reset. The flexible sealing material 97 is arranged at the side bottom to seal the removal unit 90.

Fourth Embodiment: Grey Hair Removal Component

The grey hair removal component of the present disclosure includes a sensing unit, at least one identification unit and a grey hair removal unit. FIGS. 5*a*-5*d* show schematic diagrams of the arrangement positions of the units in the grey hair removal component according to the fourth embodiment of the present disclosure.

Figure 5A:
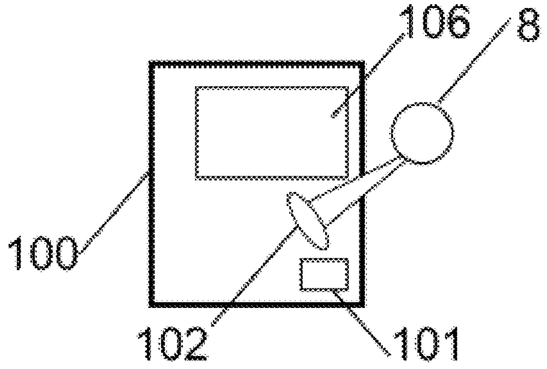
FIG. 5*a*-5*d* show schematic diagrams of grey hair removal components according to a fourth embodiment of the present disclosure.

In the preferred embodiment with reference to FIG. 5*a*, a sensing unit 101, an identification unit 102, and a removal unit 106 are arranged at the end of the grey hair removal component 100, and the identification unit 102 and the removal unit 106 point to the same operation micro-area. When the grey hair 8 is found, the removal unit 106 is driven to cut off the grey hair 8 from the root through the window.

Figure 5B:
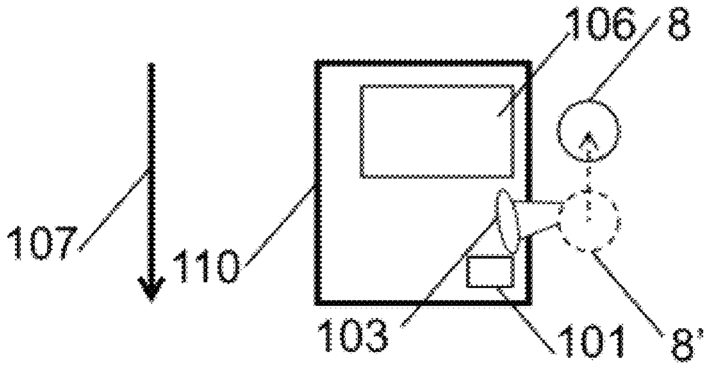

In the embodiment with reference to FIG. 5*b*, the sensing unit 101, the identification unit 103, and the removal unit 106 are arranged at the end of the grey hair removal component 110, and the identification unit 102 and the removal unit 106 point to different operation micro-regions. When the grey hair removal component 110 moves forward at a constant speed (a movement direction 107), the identification unit 103 identifies a grey hair 8' in the operation micro-area, and the removal unit 106 responds after a preset delay time, and the relative position of the grey hair 8' at this time is the position where the grey hair 8 facing the removal unit 106, and the removal unit 106 removes the hair through the window.

Figure 5C:
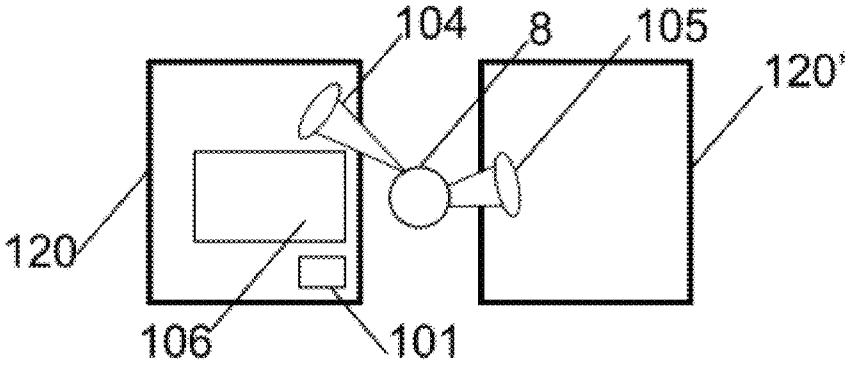

In the embodiment with reference to FIG. 5*c*, the sensing unit 101, the removal unit 106, and the identification unit 104 are arranged at the end of the housing of the grey hair removal component 120, and the identification unit 105 is arranged at the end of the opposite housing, that is, being located in the housing of the grey hair removal component 120'. When the identification unit 104 or 105 finds the grey hair 8, the removal unit 106 is driven to cut off the grey hair 8.

Figure 5D:
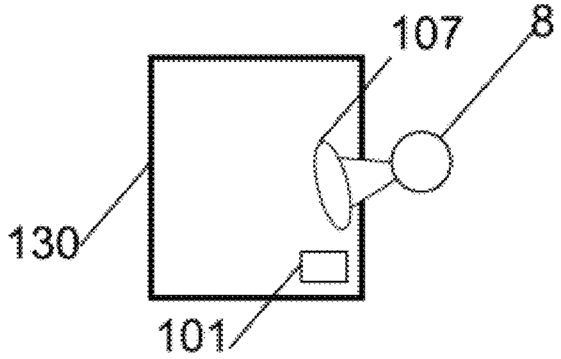

In the embodiment with reference to FIG. 5*d*, the sensing unit 101 is arranged at the end of the grey hair removal component 130, the identification unit and the removal unit share a focusing lens 107, low-intensity light is used for identification, and when the grey hair 8 is found, the light intensity of the light source (not shown) is increased to cut off the grey hair 8.

Fifth Embodiment: Grey Hair Removal Components

Figure 6A:
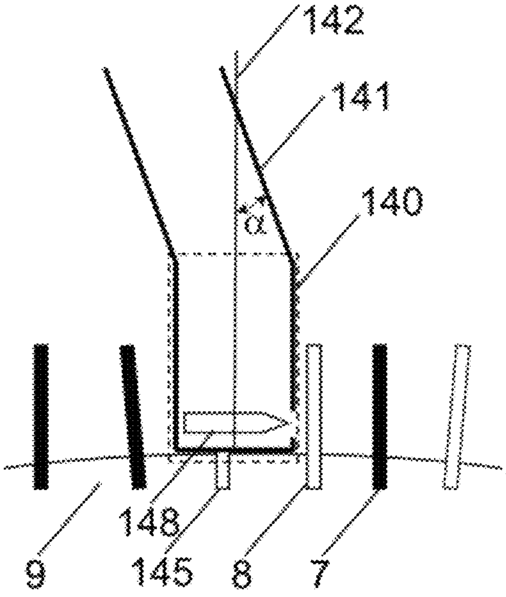
FIG. 6*a*-6*b* show schematic diagrams of grey hair removal components according to a fifth embodiment of the present disclosure.
Figure 6B:
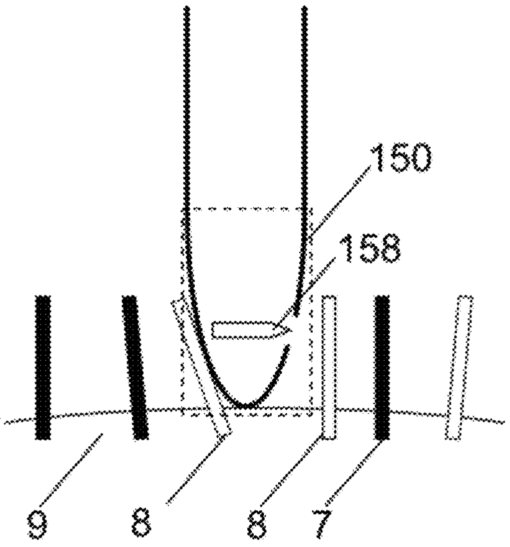

FIGS. 6*a*-6*b* show schematic diagrams of the shapes of the end of the housing in the grey hair removal component according to the fifth embodiment of the present disclosure. In the embodiment with reference to FIG. 6*a*, the end of the grey hair removal component is a square end head 140 which contacts the scalp across a large area and has a larger space at the bottom. The identification unit (not shown) and the removal unit 148 are arranged closer to the scalp 9, and the residual roots of the grey hair 8 are shorter after removal. With the square end head, only the grey hair 8 beside the component 140 is removed, while the grey hair 145 in the scalp area covered by the component 140 itself cannot be removed.

According to the design of the grey hair removal component, the end head 140 is the operation area of each unit, and is basically perpendicular to the scalp surface 9 during operation. The portion above the end head is usually perpendicular to the scalp, but it is possible to have an angle α between the upper portion 141 of the end head and the vertical line 142 of the scalp surface, as shown in FIG. 6*a*.

In the embodiment with reference to FIG. 6*b*, the end of the grey hair removal component is a tapered end head 150 which allows all hairs to be arranged on both sides of the end head 150 and to be not covered by the end head 150. Due to a small portion of the tapered end head directly contacting the scalp, the identification unit (not shown) and the removal unit 158 are usually only arranged relatively far from the scalp 9, so the residual roots of the grey hair 8 after removal are longer than that with a square end head.

Sixth Embodiment: Grey Hair Removal Comb

The sixth embodiment of the present disclosure shows a grey hair removal comb 200 including a body 208 and comb fingers 202, and at least one comb finger is the grey hair removal component as described above. Using the grey hair removal comb of the present disclosure, grey hair can be removed while combing the hair daily, leaving behind only colored hair.

Figure 7:
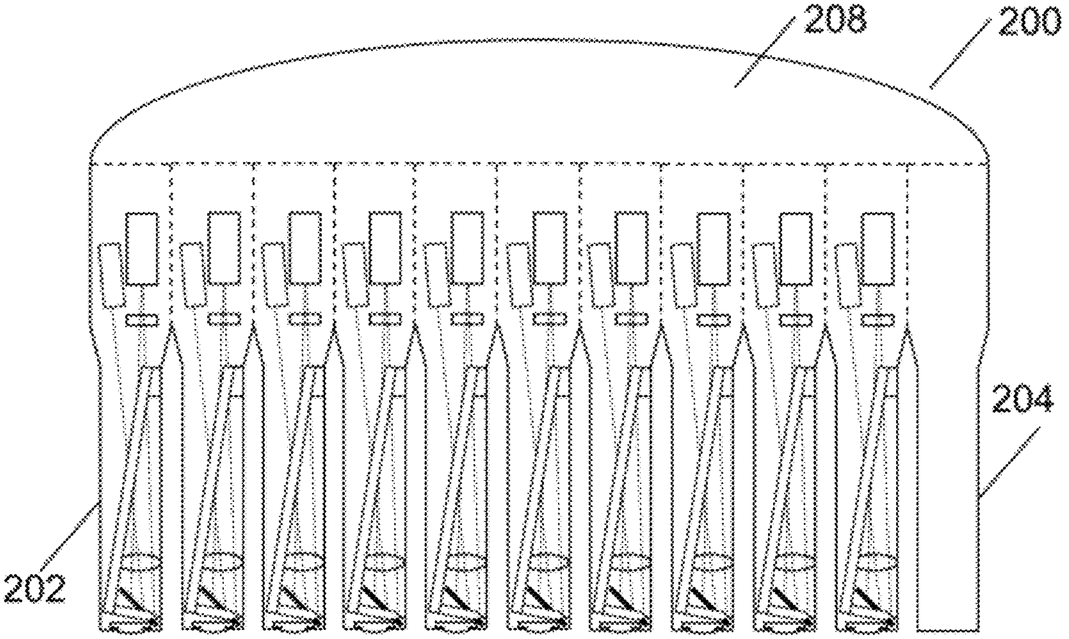
FIG. 7 shows a schematic diagram of a grey hair removal comb according to a sixth embodiment of the present disclosure.

According to one embodiment of the present disclosure, the grey hair removal components 202 has the upper portion of the housing wider than the lower portion, and are connected in parallel to form a grey hair removal comb 200, as shown in FIG. 7. Each grey hair removal component 202 is a comb finger of the grey hair removal comb 200, and the lower ends of the comb fingers are aligned.

For example, each grey hair removal component 202 includes a sensing unit 0 as shown in FIG. 2, an identification unit 10 as shown in FIG. 3*a* (the lower end is changed to a square end head), and a removal unit 90 as shown in FIG. 4*h*. The comb finger 204 at the far side of the grey hair removal comb 200 does not contain any operation unit.

The grey hair removal comb is powered by a power supply module (not shown), which is arranged in the body, also called as the comb backbone 208, and introduced from the upper dashed area of each grey hair removal component 202 to supply power to the grey hair removal component 202.

Seventh Embodiment: Grey Hair Removal Comb

Figure 8:
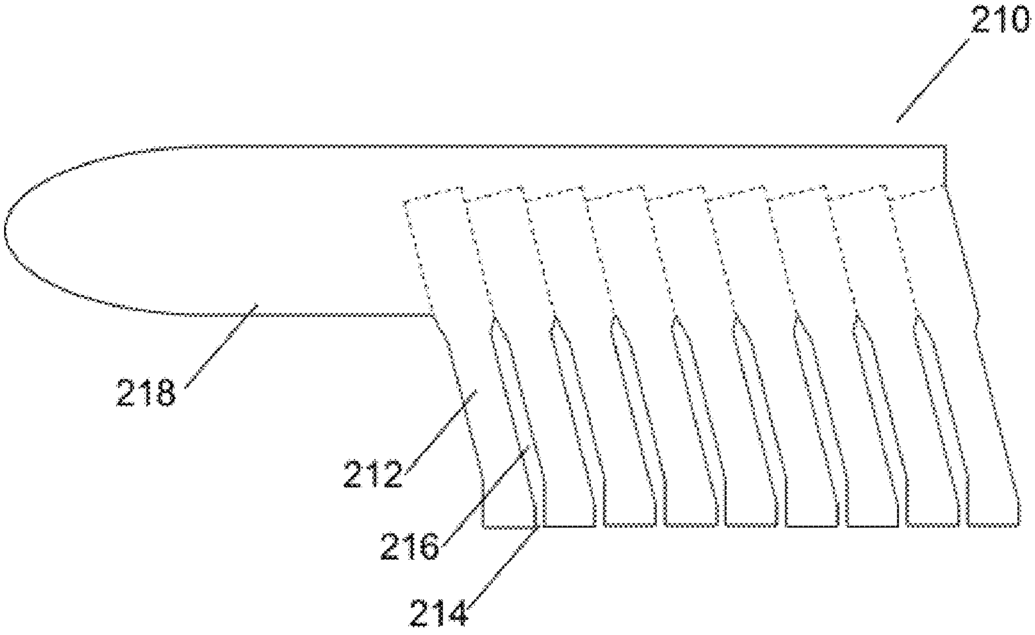
FIG. 8 shows a schematic diagram of a grey hair removal comb according to a seventh embodiment of the present disclosure.

According to another embodiment of the present disclosure, the grey hair removal comb 210 includes parallel grey hair removal components 212 as comb fingers thereof, as shown in FIG. 8. Each comb finger 212 is bent at its lower end, and the surfaces of the lower ends of all comb fingers are on a plane. The gap 214 between the comb fingers at the end surface (the scalp surface when in use) is the width of the operation micro-area, the spacing between the comb fingers is enlarged at the upper width 216, so that the rest of the hair (including the grey hair not on the scalp surface) can smoothly pass through the grey hair removal comb 210. The grey hair removal comb 210 is powered by a battery (not shown) arranged in a handle 218, for example.

Eighth Embodiment: Grey Hair Removal Comb

Figure 9:
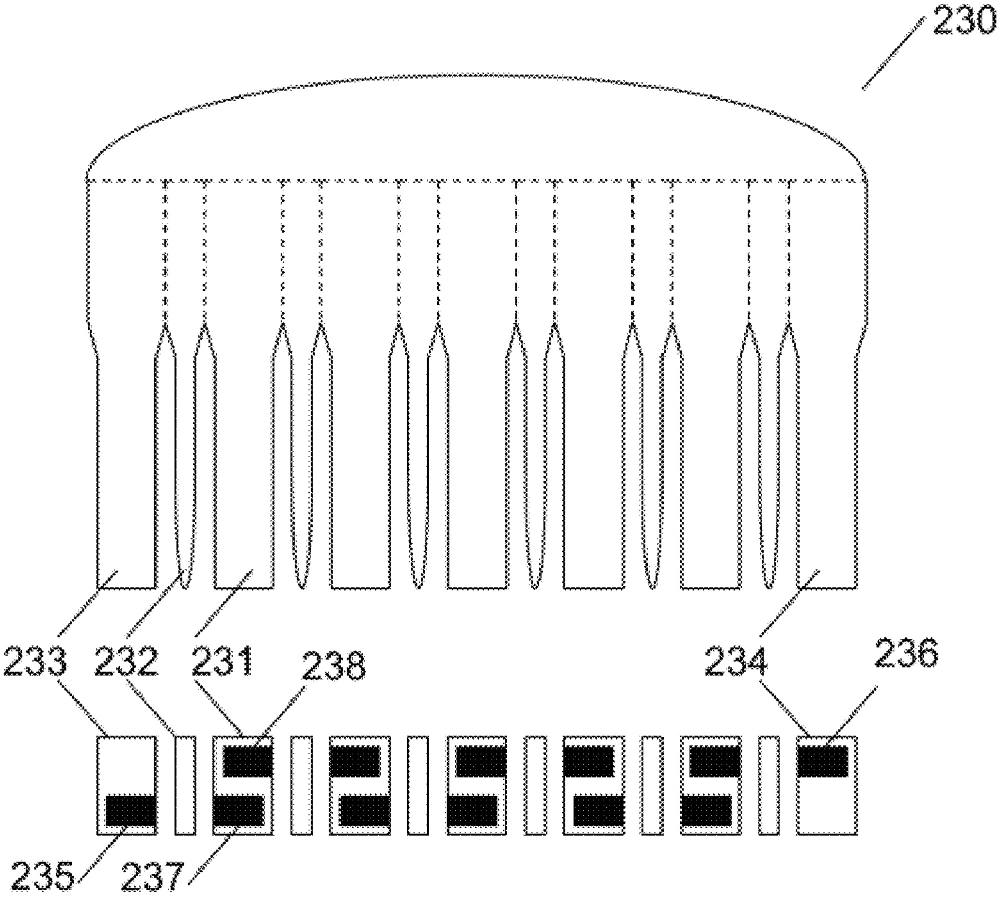
FIG. 9 shows a schematic diagram of a grey hair removal comb according to an eighth embodiment of the present disclosure.

According to another embodiment of the present disclosure, the grey hair removal comb 230 includes comb fingers 231 with square end heads and comb fingers 232 with tapered end heads, as shown in FIG. 9. The comb fingers 232 with the tapered end heads have a small width, with no grey hair removal unit arranged inside, but the removal units 235 and 237 are arranged, on both sides thereof, in the comb fingers 233 and 231 with the square ends respectively. The two comb fingers 233 and 234 at both edges of the grey hair removal comb 230 only need one removal unit, namely removal units 235 and 236, respectively. The remaining comb finger 231 with the square end heads contain two removal units 237 and 238 which are staggered back and forth along the scanning direction, and performing cutting respectively toward the left (for 237) and the right (for 238) to cut off grey hair during operation.

Ninth Embodiment: Digital Control Grey Hair Removal System

The tenth embodiment of the present disclosure provides a digital control grey hair removal system including a controlled robotic arm and at least one grey hair removal component as described above arranged on the robotic arm. Combining the grey hair removal component with the robotic arm can realize automatic and efficient removal of a grey hair.

Figure 10:
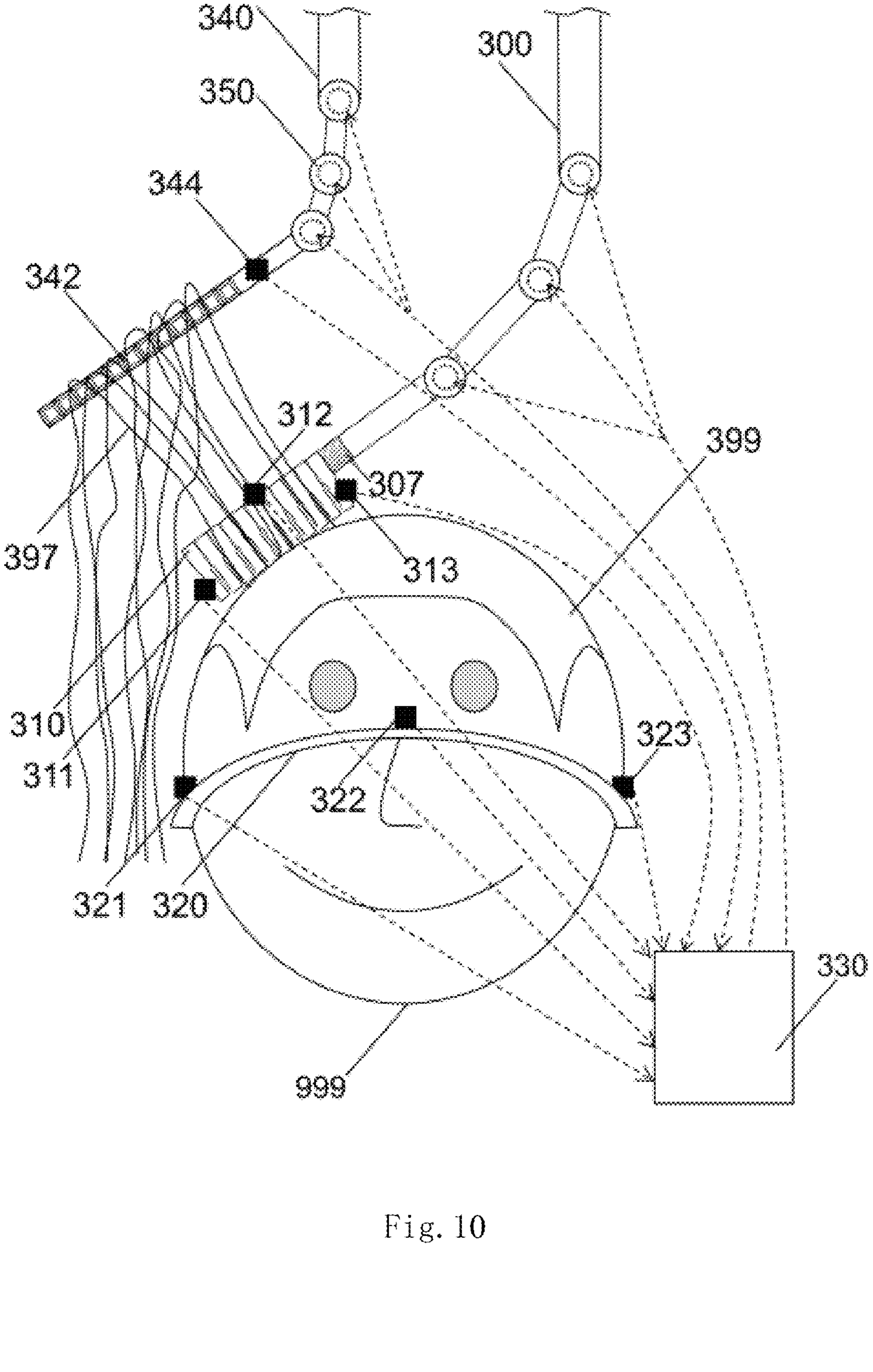
FIG. 10 shows a schematic diagram of a digital control grey hair removal system according to a ninth embodiment of the present disclosure.

According to a preferred embodiment of the present disclosure, grey hair removal components or a grey hair removal comb 310 can be connected to the robotic arm body 300 having 3 to 6 degrees of freedom, each of which is achieved by an independently driven joint 350, as shown in FIG. 10.

According to a embodiment of the present disclosure, the system includes a digital control subsystem used to control the robotic arm to scan at a determined speed and direction and to implement a grey hair removal process shown in FIG. 1.

In one embodiment, the digital control subsystem further drives the movement of each grey hair removal component based on the signal from the sensing unit in the grey hair removal component, so that the end of each grey hair removal component is in contact with the scalp to perform grey hair identification and removal.

According to a embodiment of the present disclosure, based on the actual position data of the user's scalp 399 and the actual position data of the grey hair removal component or the grey hair removal comb 310, the digital control subsystem 330 generates a posture control signal for the robotic arm body and control signals for the scanning area and direction of the grey hair removal comb. Based on the signals, the robotic arm body 300 drives the grey hair removal component or the grey hair removal comb 310 to scan the scalp 399 to remove the grey hair. During scanning, the grey hair removal component or grey hair removal comb 310 is kept at a large angle relative to the scalp 399.

Before starting to remove grey hair, a positioners 320 is fixed at the user's head 999. The positioner 320 includes three signal transmitting/receiving points 321, 322, and 323 to realize the positioning of the head 999. The positioner 320 is fixed at the nose, cheekbones, zygomatic arch, and ear regions of the user's head. Three signal transmitting/receiving points 311, 312, and 313 are fixed at the grey hair removal component or grey hair removal comb 310.

A signal transmitting/receiving base point (not shown) is fixed on a wall to determine the actual position data of the head 999 and the grey hair removal component or the grey hair removal comb 310. Signal communication between all signal transmitting/receiving points and the signal transmitting/receiving base point is performed by using electromagnetic waves, and the position data is determined according to the direction, intensity and phase of the electromagnetic waves. The position data is used to correct the position of the robotic arm body 300. When the position of the head 999 changes too much, a rescan signal can also be sent.

The only thing contact with the scalp 399 is the grey hair removal component or the grey hair removal comb 310 which is connected to the robotic arm body 300 by a movable connector 307. When the grey hair removal component or the grey hair removal comb 310 is entangled or wrapped with the hair, it is disconnected from the robotic arm body 300. The grey hair removal component or the grey hair removal comb 310 is powered by the robotic arm body 300. The robotic arm body 300 stops when it encounters resistance. A camera (not shown) is arranged on the robotic arm body 300, and an emergency power-off button (not shown) is installed for the entire system.

According to another embodiment of the present disclosure, the digital control grey hair removal system can employ two robotic arms 300 and 340. The robotic arm body 340 is connected to the comb 342 for combing the hair 397. According to the actual position data of the comb 342, the digital control subsystem 330 sends a signal to command the robotic arm 340 to cooperate with the robotic arm 300 to remove grey hair. Signal communication between the signal transmitting/receiving point 344 of the comb 342 and the signal transmitting/receiving base point is performed by electromagnetic waves.

According to another embodiment of the present disclosure, the grey hair removal unit and the identification unit of the grey hair removal component are used separately, the robotic arm 300 drives movement of the grey hair removal component, and the identification unit therein performs scanning and records three-dimensional coordinates of all grey hairs on the scalp surface, which then are input into the digital control subsystem 330, the digital control subsystem 330 commands the robotic arm to drive movement of the grey hair removal component, and the removal unit therein removes the grey hairs at the known coordinates.

According to another embodiment of the present disclosure, the embodiment enables permanent removal of a grey hair. The grey hair removal component or the grey hair removal comb 310 controlled by the digital control subsystem 330 pauses for a few seconds at each grey hair growth point, allowing the grey hair removal unit 50 as in embodiment 7 contained by the grey hair removal component or the grey hair removal comb 310 to destroy a grey hair follicle.

What is claimed is:

1. A grey hair removal comb, comprising a body and a plurality of grey hair removal comb fingers, wherein the grey hair removal comb finger comprises a grey hair removal component comprising at least one housing, a sensing unit arranged at a first end of the housing, and at least one identification unit and at least one grey hair removal unit arranged in the housing;

wherein the sensing unit, identification unit, and grey hair removal unit of the grey hair removal component act on an operation micro-area on the scalp surface;

wherein the length and width of the operation micro-area are in the range of 0.09~2 mm;

wherein the sensing unit responds to contact of the component with the scalp and outputs a start signal;

wherein each identification unit, in response to the start signal, identifies a grey hair in the operation micro-area, outputting a removal signal, and wherein a negative signal stops operations of each identification unit;

wherein each grey hair removal unit, in response to the removal signal after a preset delay time, removes the identified grey hair in one action; and wherein only if the grey hair removal components of the grey hair removal comb are in contact with the scalp do the sensing units of the grey hair removal components make the identification units and the grey hair removal units of the grey hair removal components act, whereas for the other grey hair removal components of the grey hair removal combs not in contact with the scalp, the sensing units of the grey hair removal components do not make the identification units and the grey hair removal units of the grey hair removal components act.

2. The grey hair removal comb according to claim 1, wherein the housing is provided with windows at a side wall close to the first end of the housing; and each identification unit is configured to identify the grey hair through its window, and the grey hair removal unit is configured to remove the identified grey hair through its window.

3. The grey hair removal comb according to claim 2, wherein each identification unit includes a first light source, an optical element, and a spectral sensor and/or an image sensor, wherein the optical element is arranged to reflect the light emitted by the first light source out of its window, and the light from the window is reflected to the spectral sensor or the image sensor.

4. The grey hair removal comb according to claim 3, wherein the grey hair removal unit further comprises a second light source and a focusing lens which focuses the light generated by the second light source to the identified grey hair to remove the grey hair.

5. The grey hair removal comb according to claim 3, wherein the grey hair removal unit further comprises a pulse generating unit that generates pulses in response to the removal signal to enable the first light source to output a light beam with an intensity for removing the grey hair.

6. The grey hair removal comb according to claim 2, wherein a flexible or elastic sealing material is arranged at the window of the housing.

7. The grey hair removal comb according to claim 1, wherein each identification unit includes a light source module, an information collection module, and an identification module.

8. The grey hair removal comb according to claim 7, wherein each identification module comprises a hair color identification module and a shape identification module.

9. The grey hair removal comb according to claim 1, wherein the grey hair removal unit includes an energy emission module and a focusing module, wherein the energy emission module includes a combination of one or more of light, electrical, magnetic, sound, and thermal energy emission modules.

10. The grey hair removal comb according to claim 1, wherein the grey hair removal unit further comprises a drive unit and a removal actuator, the drive unit driving the removal actuator to protrude from its window or be kept in the housing.

11. The grey hair removal comb according to claim 10, wherein the driving unit comprises a driving module which is an electrostatic driver, an electromagnetic driver, a piezoelectric driver or an inverse piezoelectric driver.

12. The grey hair removal comb according to claim 1, wherein the grey hair removal unit comprises a blade that translates or rotates.

13. The grey hair removal comb according to claim 1, wherein the grey hair removal unit further comprises a pulse generating unit for generating voltage pulses and a microneedle for applying the pulses.

14. The grey hair removal comb according to claim 1, wherein the grey hair removal component comprises a plurality of identification units arranged in the same housing or arranged in adjacent housings.

15. The grey hair removal comb according to claim 1, wherein the sensing unit is one or more of a contact switch, a pressure sensor, a heat inductor, an infrared sensor, a resistance detector, a capacitance detector, an electromagnetic inductor, or a sound wave recognizer.

16. A grey hair removal comb according to claim 1, wherein the grey hair removal unit includes a piezoelectric driver or an inverse piezoelectric driver, one end of which is fixed to the body, and the other end of which is fixed with a blade or fixed with the blade via a lever.

17. The grey hair removal comb according to claim 1, wherein the grey hair removal comb further comprises a plurality of conventional comb fingers which are arranged at intervals with the grey hair removal comb fingers.

18. A digital control grey hair removal system, comprising:

a controlled robotic arm;

a digital control subsystem used to control scanning speed and direction of the robotic arm; and a grey hair removal comb according to claim 1 arranged on the robotic arm.

19. A digital control grey hair removal method, wherein the grey hair removal component according to claim 1 is used, a dataset of three-dimensional coordinates of the entire scalp surface is obtained by sensing the scalp with digital positioning or scanning, and the at least one identification unit and the removal unit respectively distinguish hair color and remove grey hair by using the dataset of three-dimensional coordinate data as digital scan coordinates.

20. The grey hair removal comb according to claim 1, wherein the identification unit is configured to determine identify grey hair utilizing a red blue green (RBG) color model.

* * * * *